(12) United States Patent
Bader et al.

(10) Patent No.: US 6,676,970 B2
(45) Date of Patent: Jan. 13, 2004

(54) SUBCUTANEOUS OSTEOPOROSIS COMPOSITIONS

(75) Inventors: Rainer Bader, Wachenheim (DE); Petra Bastian, Regensburg (DE); Achim Goepferich, Sinzing (DE); Wolfgang Roedel, Heidelberg (DE); Gerhard Winter, Dossenheim (DE)

(73) Assignee: Hoffman-La Roche Inc., Nutley, NJ (US)

( * ) Notice: Subject to any disclaimer, the term of this patent is extended or adjusted under 35 U.S.C. 154(b) by 129 days.

(21) Appl. No.: 09/848,638

(22) Filed: May 3, 2001

(65) Prior Publication Data

US 2001/0053388 A1 Dec. 20, 2001

(30) Foreign Application Priority Data

May 5, 1922 (DE) .......................... 100 21 917

(51) Int. Cl.[7] .................... A61K 47/38; A61K 47/36; A61K 31/663
(52) U.S. Cl. .................... 424/488; 424/423; 424/422; 424/484
(58) Field of Search ................ 424/423, 422, 424/484, 488; 514/108

(56) References Cited

U.S. PATENT DOCUMENTS

| | | | |
|---|---|---|---|
| 4,446,052 A | * | 5/1984 | Sunberg et al. .......... 252/315.1 |
| 4,666,895 A | * | 5/1987 | Bosies et al. ............ 514/108 |
| 4,719,203 A | | 1/1988 | Bosies et al. |
| 4,777,163 A | | 10/1988 | Bosies et al. |
| 4,922,077 A | | 5/1990 | Gordon |
| 4,971,958 A | | 11/1990 | Bosies et al. |
| 5,002,937 A | | 3/1991 | Bosies et al. |
| 5,543,561 A | * | 8/1996 | Zilch et al. ............... 562/13 |
| 5,652,227 A | * | 7/1997 | Teronen et al. ............. 514/75 |
| 5,662,918 A | * | 9/1997 | Winter et al. ............ 424/423 |
| 5,780,455 A | * | 7/1998 | Brenner et al. ........... 514/108 |
| 6,225,294 B1 | * | 5/2001 | Daifotis et al. ........... 514/108 |

FOREIGN PATENT DOCUMENTS

| | | |
|---|---|---|
| DE | 42 44 422 | 6/1994 |
| DE | 42 44 423 | 6/1994 |
| DE | WO 00/61111 | 10/2000 |
| EP | 0 094 714 | 11/1983 |
| EP | 0 449 405 | 10/1991 |
| EP | 252 504 | 1/1998 |
| WO | Wo 94/02492 | 2/1994 |

OTHER PUBLICATIONS

Remington's Pharmaceutical Sciences, Eighteenth Edition, 1990, pp 1286–1308.*
Ash, M. and I.: Handbook of Pharmaceutical Additives. Gower, 1995, 887f., 915–918.
Ostovic et al., Drug Development and Industrial Pharmacy, 21(10), 1157–1169 (1995).

* cited by examiner

*Primary Examiner*—Thurman K. Page
*Assistant Examiner*—Rachel M. Bennett
(74) *Attorney, Agent, or Firm*—George W. Johnston; Patricia S. Rocha-Tramaloni; Bernard Lau

(57) ABSTRACT

The invention is concerned with a pharmaceutical preparation for subcutaneous, parenteral administration, which contains bisphosphonic acids or their salts as the active substance, as well as the production of this preparation. By means of the preparation in accordance with the invention it is possible to administer locally relatively high concentrations of bisphosphonates without the occurrence of incompatibilities.

48 Claims, No Drawings

US 6,676,970 B2

SUBCUTANEOUS OSTEOPOROSIS COMPOSITIONS

BACKGROUND OF THE INVENTION

The invention is concerned with a pharmaceutical preparation for subcutaneous, parenteral administration, which contains bisphosphonic acids or their salts as the active substance, as well as the production of this preparation. By means of the preparation in accordance with the invention it is possible to administer locally relatively high concentrations of bis-phosphonates without the occurrence of incompatibilities.

Bisphosphonates and their salts have been in use for years as highly effective medicaments for the treatment of various disorders of bone metabolism. Thus, a variety of bisphosphonates are used for the treatment of hypercalcaemia, malignant bone growth disorders (metastatic bone disease) as well as osteoporosis, while others are in clinical development. Clodronate, ibandronate, tiludronate, etidronate, alendronate, risedronate, zoledronate among others can be named as examples. Bisphosphonates are used in a broad dosage range taking into consideration the widest variety of factors, especially the medical indication. Thus, parenteral preparations for intravenous infusion and injection are preferably made available and utilized.

The subcutaneous, parenteral administration of clinically relevant amounts of bisphosphonic acids or their salts is, however, problematic. Inflammations, pains and necroses occur when bisphosphonate solutions are administered subcutaneously in therapeutically relevant concentrations, which are, for example, well tolerated in the case of intravenous administration. Of course, the subcutaneous administration is especially attractive in many respects, because this mode of administration is perceived by the majority of patients to be much more pleasant than intravenous administration. It can be performed by medical auxiliaries or by patients themselves.

The pharmacokinetic differences which can occur in the case of subcutaneous administration vis-à-vis intravenous administration are not of significance for the fields of indication osteoporosis and osteoporosis prophylaxis which are at the centre of interest, since bis-phosphonates display their activity after binding to bones, are accumulated there for a very long time and therefore their residence times in the blood after injection or also after oral administration are only of secondary importance.

Thus, only a few, not completely satisfactory proposals for the development of subcutaneously usable bisphosphonate preparations have hitherto become known.

Difficulty soluble zinc and magnesium salts of 1,1-bisphosphonic acids are described in DE 42 44 422 A1, with the object of releasing therapeutically relevant amounts of active substance slowly by dissolution from a local depot.

However, for various reasons this principle is not well suited to achieve a significantly improved compatibility. Thus, even if the dissolution kinetic is altered a good compatibility does not, however, result, since a particulate system is formed by the difficultly soluble salt. It has been established that this not only has numerous disadvantages upon administration, but also leads to additional difficulties. From the technological viewpoint not only the production, dosing and decantation, but also the storage, quality control and quality guarantee of such systems is very difficult. Particulate systems are mainly suspensions which are physically unstable and, for this reason, in the case of short-term storage already undergo changes which are relevant to quality. As mentioned above, the administration of such particulate systems is not simple. Thus, dosing problems, which are caused by phase separation or sedimentation, can occur immediately upon administration. The obstruction of injection needles by suspension particles is likewise a problem which has to be taken into consideration seriously.

The subcutaneous administration of difficultly soluble particles is not optimal also from the toxicological viewpoint. The presence of foreign particles induces specific and non-specific defence mechanisms which lead to diverse reactions, especially to local cellular changes. Phagocytes accumulate, other cells accompany the degradation and an encapsulation of the foreign particles may occur. In summary, particulate systems lead to generally undesired reactions which decrease compatibility.

On the other hand, water-soluble calcium salts of ibandronate for the production of medicaments are described in DE 42 44 423 A1. These eliminate the disadvantages of difficultly soluble salts and, on the basis of a lower solubility than the usual alkali or ammonium salts, they should have a better tissue compatibility than these without exhibiting the disadvantages of the suspensions.

This formulation strategy is, however, not completely conclusive and in practice does not lead to the desired, medically relevant improvement in compatibility. As a molecular dispersed solution ("true solution" in the physicochemical sense) is present, then its concentration of dissolved active substance (e.g. 1 mg/ml) alone determines the compatibility and not on the other hand the saturation solubility. While the saturation solubilities of e.g. $Na^+$ and $Ca^{2+}$ salts of bisphosphonates, especially ibandronate, differ significantly, their individual physiological irritating effects are on the other hand the same in the case of the same dissolved concentration.

It has been established that the achievable compatibility limits or active substance concentrations of water-soluble $Ca^{2+}$ salts, which are well tolerated after subcutaneous administration, are so low that they are not usable in practice. In particular, the treatment interval of only one or a few injections every three months, which is especially desirable and attractive from the viewpoint of patients and of medical personnel, can therefore not be realized.

The underlying purpose of the invention accordingly lay in the provision of pharmaceutical preparations suitable for subcutaneous administration which contain bisphosphonic acids or their physiologically compatible salts and with which it is possible to administer locally high, therapeutically relevant concentrations of bisphosphonates compatibly such that medically significant treatment regimens with administrations at long time intervals ($\geq 4$ weeks) are possible.

SUMMARY OF THE INVENTION

The problem of the invention is solved by an aqueous pharmaceutical preparation which contains the active substance or the active substance mixture and at least one compound which inhibits a diffusion of the active substance in the tissue, with the active substance being present in dissolved form in the preparation and the active substance and diffusion-inhibiting compound being selected such that the pharmaceutical preparation contains no solid particulate components. If desired, other usual pharmaceutical carriers and/or adjuvants, which, however, should not form particles, are present in the preparation.

The invention is concerned with a pharmaceutical preparation for subcutaneous, parenteral administration, which contains bisphosphonic acids or their salts as the active substance, as well as the production of this preparation. By means of the preparation in accordance with the invention it is possible to administer locally relatively high concentrations of bis-phosphonates without the occurrence of incompatibilities. The pharmaceutical composition of this invention comprises an aqueous gel having a viscosity of ≧220 mPa*s containing as an active ingredient for combating osteoporosis a bisphosphonate acid or its pharmaceutically acceptable salt dissolved in aqueous solution and a polymeric gel forming agent capable of inhibiting diffusion of the active ingredient with human tissue. This composition is in a dosage form for subcutaneous administration.

DETAILED DESCRIPTION OF THE INVENTION

In a preferred embodiment the present invention comprises a gel-like, aqueous pharmaceutical preparation for subcutaneous administration containing bisphosphonic acids or their physiologically acceptable salts, characterized in that the pharmaceutical preparation contains at least one compound which inhibits the diffusion of the active substance in the tissue, with the active substance being present in dissolved form in the preparation and the preparation having a viscosity ≧220 mPa*s.

In accordance with a preferred embodiment of this invention, the pharmaceutical composition comprises an aqueous gel having a viscosity of ≧220 mPa*s in a unit dosage form suitable for subcutaneous administration to the tissue of human patients, said gel containing as an active ingredient 200–1000 μg, preferably 200–300 μg, of a bisphosphonate acid or its pharmaceutically acceptable salt, which are active in combating osteoporosis dissolved in an aqueous solution, and from about 0.01%–15% by weight based upon the weight of the aqueous gel, of a polymeric gel forming agent capable of inhibiting diffusion with human tissue. In accordance with another embodiment of this invention, the composition contains 200–1000 μg, preferably 200–300 μg of the active substance or active substance mixture, 0.5 mg of a calcium salt and 15 mg of a cellulose derivative or alginate in 1 ml of water. In accordance with still another embodiment of this invention, the composition contains 1 mg of the active substance or active substance mixture, 1 mg of a calcium salt and 50 mg of a cellulose derivative or alginate in 1 ml of water.

This invention also includes a method for combating osteoporosis by subcutaneous administering to the tissue of a human patient an aqueous gel having a viscosity of ≧220 Pa*s containing as an active ingredient a bisphosphonate acid or its pharmaceutically acceptable salt active in combating osteoporosis dissolved in an aqueous solution and present in said gel in an effective amount to combat osteoporosis and a polymeric gel forming agent capable of inhibiting diffusion of said active ingredient into human tissue. The invention also includes a method for subcutaneous administration of osteoporosis bisphosphonates combating agent by utilizing the compositions of this invention.

The addition of the diffusion-inhibiting substance prevents on the basis of specific and non-specific interactions with the active substance and its counter-ions (such as e.g. $Na^+$, $Ca^{2+}$ etc.) the bisphosphonic acids or their salts from causing incompatibility symptoms, such as e.g. irritations, in the tissue after subcutaneous administration.

The diffusion-inhibiting substances are in the meaning of the invention preferably hydrogel-forming substances and other non-particulate matrices, preferably natural and synthetic polymers.

In accordance with the invention any conventional pharmaceutically or physiologically acceptable polymer and gel forming agents can be utilized to produce the aqueous gels of this invention. These gel forming agents will inhibit the diffusion of the active ingredient with human tissue when the composition is administered to a human patient subcutaneously. These conventional polymeric gel forming agents include cellulose derivatives, alginic acid derivatives, dextrans, hyaluronic acids, dermatan and heparan sulphates, gelatins, collagen, polyvinylpyrrolidone, polyvinyl alcohol, poly(meth)acrylic acids, poly(meth)acrylates and/or their derivatives. Derivatives are chemically modified entities obtained by amidation, alkylation, carboxymethylation, addition of fatty acid units or addition of polyethyleneglycol-units (so called 'pegylation'). To get the necessary gel forming properties the polymers additionally may be cross-linked by e.g. glutardialdehyde. In case of acidic compounds (alginic acid, polymethacrylates) derivatives are also their salts (such as ammonium-, barium-, magnesium-, calcium-salt). These compounds are known in the art and described for example in Ash, M. and I.: Handbook of Pharmaceutical Additives. Gower, 1995, 887f.; 915–918; Fiedler, H. P.: Lexikon der Hilfsstoffe. ecv, 1998; Kibbe, A. H.: Handbook of Pharmaceutical Excipients. 3rd ed., Pharmaceutical Press, 2000. Preferably, the natural polymer is selected from the group consisting of cellulose derivatives, alginic acid derivatives, dextrans, gelatines, collagen, hyaluronic acids and/or dermatan and heparan sulphates. The cellulose derivatives are the preferred diffusion-inhibiting substances in the meaning of the invention. In the case of the cellulose derivatives there preferably come into consideration the soluble alkyl- or hydroxyalkylcellulose derivatives, such as e.g. hydroxymethylcellulose (HMC), hydroxyethylcellulose (HEC), hydroxypropylcellulose (HPC), methylhydroxyethylcellulose (MHEC), hydroxypropylmethylcellulose (HPMC), carboxymethylcelluose (CMC), methylcellulose (MC) or their mixtures.

The term "alkyl", alone or in combination, means a straight-chain or branched-chain alkyl group containing a maximum of 7, preferably a maximum of 4, carbon atoms, e.g., methyl, ethyl, n-propyl, 2-methylpropyl (iso-butyl), 1-methylethyl (iso-propyl), n-butyl, and 1,1-dimethylethyl (t-butyl), preferably methyl and ethyl.

A more preferred natural polymer is sodium carboxymethylcellulose. Another preferred natural polymer is alginate.

In another preferred embodiment of the present invention, the synthetic polymer is selected from the group consisting of poly(meth)acrylic acids, poly(meth)acrylates, polyvinylpyrrolidone and polyvinyl alcohol.

In accordance with the invention the gel formers are used in concentrations which produce the viscosities which on the one hand produce the requisite diffusion inhibition and on the other hand permit the requisite injectability to human subjects. The gel former is used in concentrations of from 0.01 to 15% (w/w).

In an especially preferred embodiment of the invention sodium carboxymethylcellulose (Na CMC) is used in a concentration of from 1 to 7% (w/w), particularly of 4–6% (w/w). In another preferred embodiment alginate is used in concentrations of from 1 to 5% (w/w), especially of from 2 to 3% (w/w).

In accordance with the invention the preferred viscosities of the thickened preparations produced by means of the gel former lie in the range of ≧220 mPa*s, particularly of 350 to 1800 mPa*s, whereby the preparations must be administerable by means of suitable injection needles.

In a further especially preferred embodiment, calcium salts are added to the composition to produce calcium ions (final concentration of from 1 to 20 mM, preferably from 5 to 15 mM), with these being preferably added in the form of calcium chloride.

Bisphosphonic acids are well known for combating osteoporosis. These not only include bisphosphonic acids but their pharmaceutically acceptabel salts and esters. These compounds and their method of administration for combating osteoporosis have been described throughout the literature. However, there has not been described an effective means for subcutaneously administering these antiosteoporosis active bisphosphonic acids, salts and esters to human patients. The composition of this invention in its aqueous gel form provides a means and method for subcutaneously administering these compositions subcutaneously to human patients. By combating osteoporosis, these phosphonates are useful both in the prophylaxis and treatment of osteoporosis.

Also, this invention provides a new method for subcutaneously administering these antiosteoporosis bisphosphonates to patients through subcutaneous means. In accordance with this invention, any of the conventional antiosteoporosis active bisphosphnates can be administered subcutaneously through use of the compositions of this invention so as to combat osteoporosis.

Bisphosphonic acids or their physiologically acceptable salts as pharmaceutical active substances are described for example in U.S. Pat. No. 4,666,895, U.S. Pat. No. 4,719, 203, EP-A-252,504, EP-A-252,505, U.S. Pat. Nos. 4,777, 163, 5,002,937, and U.S. Pat. No. 4,971,958. Methods for the preparation of bisphosphonic acids may be found in, e.g., U.S. Pat. Nos. 3,962,432; 4,054,598; 4,267,108; 4,327,039; 4,407,761; 4,621,077; 4,624,947; 4,746,654; 4,922,077; 4,970,335; 5,019,651; 4,761,406; and U.S. Pat. No. 4,876, 248; J. Org. Chem. 32,4111 (1967) and EP-A-252,504.

The pharmaceutically acceptable salts of bisphosphonic acids may also be employed in the instant invention. Examples of base salts of bisphosphonic acids include ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. The non-toxic, physiologically acceptable salts are preferred. The salts may be prepared by methods known in the art, such as described in European Patent Pub. No. 252,504 or in U.S. Pat. No. 4,922,077.

In a preferred embodiment of the present invention, the term "bisphosphonate" of the present invention corresponds to compounds of general formula

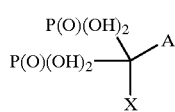

(I)

wherein A and X are independently selected from the group consisting of hydrogen, hydroxy, halogen, amino, SH, phenyl, alkyl, mono- or dialkylamino, mono- or dialkylaminoalkyl, alkoxy, thioalkyl, thiophenyl, and aryl or heteroaryl moieties selected from the group consisting of phenyl, pyridyl, furanyl, pyrrolidinyl, imidazolyl, and benzyl, wherein the aryl or heteroaryl moiety is optionally substituted with alkyl.

In the foregoing chemical formula, A can include X and X include A such that the two moieties can form part of the same cyclic structure.

The foregoing chemical formula is also intended to encompass carbocyclic, aromatic and heteroaromatic structures for the A and/or X substituents, e.g. naphthyl, quinolyl, isoquinolyl, adamantyl, and chlorophenylthio.

Preferred structures are those in which A is selected from the group consisting of hydrogen, hydroxy, and halogen, an X is selected from the group consisting of alkyl, halogen, thiophenyl, thioalkyl and dialkylaminoalkyl.

More preferred structures are those in which A is selected from the group consisting of hydrogen, hydroxy, and Cl and X is selected from the group consisting of alkyl, Cl, chlorophenylthio and dialkylaminoalkyl.

Most preferred is when A is hydroxy and X is (N-methyl-N-pentyl)amino-ethyl, i.e. ibandronate.

Examples of bisphosphonates, i.e. bisphosphonic acids and pharmaceutically acceptable salts thereof which may be employed as active ingredients in the compositions and methods for subcutaneously administering these compositions of the instant invention:

a) 4-amino-1-hydroxybutylidene-1,1-bisphosphonic acid (alendronate),
b) N-methyl-4-amino-1-hydroxybutylidene-1,1-bisphosphonic acid,
c) 4-(N,N-dimethylamino)-1-hydroxybutylidene-1,1-bisphosphonic acid,
d) 3-amino-1-hydroxypropylidene-1,1-bisphosphonic acid (pamidronate),
e) 3-(N-methyl-N-pentyl) amino-1-hydroxypropane-1,1-bisphosphonic acid (ibandronic acid),
f) [3-(N-methyl-N-pentyl) amino-1-hydroxypropane-1,1-bisphosphonic acid, monosodium salt, monohydrate] (ibandronate),
g) 1-hydroxy-3-(N-methyl-N-pentylamino)propylidene-1,1-bisposphonic acid,
h) 1-hydroxy-2-[3-pyridinyl]ethylidene-1,1-bisphosphonic acid (risedronate),
i) 4-(hyroxymethylene-1,1-bisphosphonic acid)piperidine,
j) cycloheptylaminomethylene-1,1-bisposphonic acid (cimadronate),
k) 1,1-dichloromethylene-1,1-diphosphonic acid and the dissodium salt (clodronate),
l) 1-hydroxy-3-(1-pyrrolidinyl)-propylidene-1,1-bisphosphonic acid (EB-1053),
m) 1-hydroxyethane-1,1-diphosphonic acid (etidronic acid),
n) 6-amino-1-hydroxyhexylidene-1,1-bisphosphonic acid (neridronate),
o) 3-(dimethylamino)-1-hydroxypropylidene-1,1-bisphosphonic acid (olpadronate),
p) [2-(2-pyridinyl)ethylidene]-1,1-bisphosphonic acid (piridronate),
q) (4-chlorophenyl)thiomethane-1,1-diphosponic acid (tiludronate),
r) 1-hydroxy-2-(1H-imidazol-1-yl)ethylidene-1,1-bisphosphonic acid (zolendronate).
s) [(cycloheptylamino)-methylene]-bisphosphonic acid (icadronate), and/or
t) [1-Hydroxy-2imidazo-(1,2-a) pyridin-3-ylethylidene]-bisphosphonic acid
and pharmaceutically acceptable salts thereof.

Active substances used in accordance with the invention are aminobisphosphonates, such as e.g. ibandronate, clodronate, etidronate, risedronate, zoledronate, tiludronate, pamidronate, cimadronate (YM175) and/or alendronate or their sodium or calcium salts.

The active substances are preferably used in the form of their soluble salts to which belong ammonium salts, alkali and alkaline earth salts such as sodium, potassium, calcium and magnesium salts, salts with organic bases such as dicyclohexylamine salts or salts with amino acids such as e.g. arginine or lysine. It is especially preferred to use the sodium or calcium salts.

In a more preferred embodiment of the present invention, the bisphosphonate is 3-(N-methyl-N-pentyl) amino-1-hydroxypropane-1,1-bisphosphonic acid (ibandronic acid) or pharmaceutically acceptable salts thereof, or even more preferably 3-(N-methyl-N-pentyl) amino-1-hydroxypropane-1,1-bisphosphonic acid, monosodium salt, monohydrate.

In a preferred embodiment of the invention the preparation may comprise an active substance, a calcium salt and a diffusion inhibiting compound selected from the group consisting of carboxymethylcellulose and alginate.

In a preferred embodiment of the present invention a preparation as described above may contain 200–1000 $\mu$g, preferably 200–300 $\mu$g of the active substance or active substance mixture, 0.5 mg of a calcium salt and 15 mg of a cellulose derivative or alginate in 1 ml of water. Another preferred embodiment of the present invention may comprise 1 mg of the active substance or active substance mixture, 1 mg of a calcium salt and 50 mg of a cellulose derivative or alginate in 1 ml of water.

Another aspect of the present invention relates to a process for the production of an aqueous pharmaceutical preparation for subcutaneous administration containing bisphosphonic acids or their physiologically acceptable salts as the active substance as described above, characterized by dissolving the active substance in water and subsequently adding to the solution a compound which inhibits the diffusion in the tissue or mixing the active substance and diffusion-inhibiting compound and dissolving them together in water or adding the active substance to aqueous solutions of the diffusion-inhibiting compounds. Optionally a calcium salt is added.

The invention also refers to the use of a preparation as described above for the preparation of a medicament of the treatment of osteoporosis.

The production of the pharmaceutical preparations is carried out according to conventional procedures. For example, aqueous solutions of the active substance, optionally with the addition of a calcium compound, are produced and are then treated with the diffusion-inhibiting substance so that no solid particles are present or the active substance and diffusion-inhibiting compound, optionally with the addition of a calcium compound, are admixed, and dissolved together. In a further procedural variant, aqueous solutions of the diffusion-inhibiting substances are firstly produced and to these are subsequently added the active substances, optionally with the addition of a calcium compound.

By means of the thus-produced pharmaceutical preparations it is possible to utilize bisphosphonic acids or their salts subcutaneously in a pain-free and medically-safe manner.

Thus, e.g. by means of the preparations in accordance with the invention 1 mg of an active substance can be administered not only at intervals of 3 months or in appropriate aliquots every four weeks, but also in substantially smaller amounts every second, third, etc. day. In a particularly preferred embodiment 200–300 $\mu$g of active substance or active substance mixture, optionally with the addition of calcium ions (7–12 mM) can be mixed with 15 mg of a diffusion-inhibiting substance, e.g. sodium carboxymethylcellulose or alginate, and administered subcutaneously every 4 weeks. In another particularly preferred embodiment 1 mg of active substance or active substance mixture, optionally with the addition of 7 mM of calcium ions, is mixed with 50 mg of a diffusion-inhibiting substance, e.g. sodium carboxymethycellulose or alginate, and administered subcutaneously at intervals of 3 months. The pharmaceutical preparation can also be administered intermittently. Thus, a threefold administration at intervals of 4 weeks can follow a pause of 3 months.

Accordingly, by means of the preparation in accordance with the invention highly concentrated doses are possible which are well tolerated after subcutaneous administration.

Furthermore, it is possible to provide the preparation in accordance with the invention so that it can be given using a multi-dose administration system (so-called pen) over a period of e.g. 4 to 6 weeks in prescribed intervals and dosages. Thereby, on pressing the button the appropriate dosage is injected once weekly in a manner which is especially simple and convenient for patients. With this, injection volumes between 25 $\mu$g and 1 ml per injection can be realized.

In accordance with the invention it is also possible to administer locally relatively high concentrations of bisphosphonates without the need to make allowances for the disadvantages resulting in the use of highly concentrated solutions or particulate systems.

The invention is illustrated in more detain in the following Examples.

EXAMPLES

Example 1

Preparations of Bisphosphonate-Containing Sodium Carboxymethylcellulose (CMC) Hydrogels Preparation Method 1

20 mg or 100 mg of the active substance are weighed into a closable glass vessel together with 5.00 g of Na CMC and made up to 100.0 g with bidistilled water. The solid components are dispersed in the closed vessel by shaking vigorously for 30 seconds. Subsequently, the mixture is stirred, initially rapidly, for example at 300 revolutions per minute, using a magnetic stirrer with a large magnetic core or using a propeller stirrer. After about 10 minutes the number of revolutions is lowered to about 10 to 20 per minute in order to avoid the inclusion of air in the swelling preparation. The temperature can be increased up to about 80° C. in order to accelerate the swelling procedure. The preparation is stirred in the closed vessel until the transparent gel is homogeneous upon flowing and appears free from agglomerations. As a rule, this state is reached after 3 days.

Preparation Method 2

20 mg or 100 mg of the active substance are made up to 95.0 g with bidistilled water and dissolved. 5.00 g of Na CMC are weighed into a closable glass vessel and treated with the substance solution. The solid components are dispersed in the closed vessel by vigorous shaking for 30 seconds. Subsequently, the mixture is stirred, initially rapidly, for example at 300 revolutions per minute, using a magnetic stirrer with a large magnetic core or using a propeller stirrer. After about 10 minutes the number of revolutions is lowered to about 10 to 20 per minute in order to avoid the inclusion of air in the swelling preparation. The temperature can be increased up to about 80° C. in order to accelerate the swelling procedure. The preparation is stirred in the closed vessel until the transparent gel is homogeneous upon flowing and appears free from agglomerations. As a rule, this state is reached after 3 days.

Preparation Method 3

20 mg or 100 mg of the active substance are weighed into a closable glass vessel together with 5.00 g of Na CMC and 100 mg of calcium chloride and made up to 100.0 g with bidistilled water. The solid components are dispersed in the closed vessel by shaking vigorously for 30 seconds. Subsequently, the mixture is stirred, initially rapidly, for example at 300 revolutions per minute, using a magnetic stirrer with a large magnetic core or using a propeller stirrer. After about 10 minutes the number of revolutions is lowered to about 10 to 20 per minute in order to avoid the inclusion of air in the swelling preparation. The temperature can be increased up to about 80° C. in order to accelerate the swelling procedure. The preparation is stirred in the closed vessel until the transparent gel is homogeneous upon flowing and appears free from agglomerations. As a rule, this state is reached after 3 days.

Preparation Method 4

20 mg or 100 mg of the active substance and 100 mg of calcium chloride are made up to 95.0 g with bidistilled water and dissolved. 5.00 g of Na CMC are weighed into a closable glass vessel and treated with the substance solution. The solid components are dispersed by vigorous shaking for 30 seconds. Subsequently, the mixture is stirred, initially rapidly, for example at 300 revolutions per minute, using a magnetic stirrer with a large magnetic core or using a propeller stirrer. After about 10 minutes the number of revolutions is lowered to about 10 to 20 per minute in order to avoid the inclusion of air in the swelling preparation. The temperature can be increased up to about 80° C. in order to accelerate the swelling procedure. The preparation is stirred in the closed vessel until the transparent gel is homogeneous upon flowing and appears free from agglomerations. As a rule, this state is reached after 3 days.

Preparation Method 5

20 mg or 100 mg of the active substance are made up to 95.0 g with bidistilled water and dissolved. This solution is poured into a glass vessel of large diameter, for example into a Petri dish with a diameter of 15 to 30 cm. 5.00 g of Na CMC are sprinkled in a thin layer on the surface of the standing liquid. The vessel is covered to prevent evaporation. The vessel must be stored without vibration until the swelling of the Na CMC has finished. After about 3 days, when the gel has swollen homogeneously, it can be transferred into another vessel and sealed.

Preparation Method 6

20 mg or 100 mg of the active substance and 100 mg of calcium chloride are made up to 95.0 g with bidistilled water and dissolved. The solution is poured into a glass vessel of large diameter, for example into a Petri dish with a diameter of 15 to 30 cm. 5.00 g of Na CMC are sprinkled in a thin layer on the surface of the standing liquid. The vessel is covered to prevent evaporation. The vessel must be stored without vibration until the swelling of the Na CMC has finished. After about 3 days, when the gel has swollen homogeneously, it can be transferred into another vessel and sealed.

Example 2

Preparations of Bisphosphonate-Containing Alginate Hydrogels

Preparation Method 1

20 mg or 100 mg of the active substance are weighed into a closable glass vessel together with 2.50 g of alginate and 100 mg of calcium chloride and made up to 100.0 g with bidistilled water. The solid components are dispersed in the closed vessel by shaking vigorously for 30 seconds. Subsequently, the mixture is stirred, initially rapidly, for example at 300 revolutions per minute, using a magnetic stirrer with a large magnetic core or using a propeller stirrer. After about 10 minutes the number of revolutions is lowered to about 10 to 20 per minute in order to avoid the inclusion of air in the swelling preparation. The temperature can be increased up to about 80° C. in order to accelerate the swelling procedure. The preparation is stirred in the closed vessel until the transparent gel is homogeneous upon flowing and appears free from agglomerations. As a rule, this state is reached after 3 days.

Preparation Method 2

2.50 g of alginate are weighed into a closable glass vessel and made up to 80.0 g with bidistilled water. The solid substance is dispersed in the closed vessel by shaking vigorously for 30 seconds and subsequently stirred, initially rapidly, for example at 300 revolutions per minute, using a magnetic stirrer with a large magnetic core or using a blade stirrer. After about 10 minutes the number of revolutions is lowered to about 10 to 20 per minute and stirring is continued overnight.

On the next day 20 g of the active substance solution (see below) are added dropwise with further stirring and stirring is continued for a further day. Thereafter, the gel is left to stand for a further 24 hours in order for the air to disappear.

Preparation of the active substance solution: 40 mg or 200 mg of the active substance and 200 mg of calcium chloride are made up to 40.0 g with bidistilled water and dissolved.

Example 3

Testing for the Subcutaneous Compatibility of an Aqueous Buffered Solution of 0.2 mg/ml Ibandronate Preparation and Filling of the Solution 1600 ml of water (water for injection) are placed in a glass beaker and 562.5 mg of ibandronate (hydrate, monosodium salt, corresponding to 500 mg of ibandronate) are dissolved therein while stirring. 21.5 mg of NaCl are added and dissolved and the pH is adjusted to a value of 6.0 by the addition of sodium acetate. Thereafter, the mixture is made up to the final volume of 2500 ml with water.

The solution is filtered through a 0.2 $\mu$m membrane and filled into ampoules. The filled ampoules are subsequently steam sterilized at 121° C./20 minutes.

Compatibility Testing

The local subcutaneous compatibility was tested using 4 male and 4 female rabbits. Each animal was given a total of 3 injections (in each case 0.5 ml/animal)—divided over 7 days—under the skin of the left side of the body. In the isolated sections the injection sites were controlled for histopathological evaluation.

Clinically the animals showed pain reactions during and after the injections.

Macroscopically all injection sites were swollen and reddened.

Histopathologically the samples (in each case 2 to 3 tissue sections from different levels of the injection region) showed dear signs of an irritation, independently of the observation period:

Transcribed, predominantly subcutaneous necroses (binding tissue/muscle tissue);

predominantly high degree inflammatory oedema site/focal haemorrhages and vasculitis;

focal inflammatory cell infiltration in different degrees of prominence.

Evaluation of the aforementioned formulation: Subcutaneously incompatible having regard to the present results.

Example 4

Testing for the Subcutaneous Compatibility of a CMC Gel Without Ibandronate (placebo)

Preparation and Filling of the Placebo Gel for an Animal Experiment 100 ml of water (water for injection) are placed in a glass beaker.

Thereafter, 12.5 g of Na carboxymethylcellulose are introduced portionwise and the volume is made up to 250 ml with water. The batch is stirred slowly with a blade stirrer for 24 hours and thereafter left to stand for a further 24 hours in order for the air to disappear.

The gel is then filled into sterilized glass syringes having a flask and rubber plunger, with the fill amount of each syringe being 0.55 g (filling via the cone). The cone of each syringe was sealed with a rubber tip cap.

The filled syringes are stood upright (i.e. with the cone upwards) and sterilized by steam scrubbing in an autoclave. A Pt100 heat conductor placed in the product solution of one syringe is used to control the sterilization time (121–123° C., 20 min., 1 bar gauge pressure).

The syringes are subsequently dried in a sterile room for 12 hours at room temperature under laminar flow and stored sealed in sterilized foil until used.

Compatibility Testing

The local subcutaneous compatibility was tested using 4 male and 4 female rabbits. Each animal was given a total of 3 injections (in each case 0.5 ml/animal)—divided over 7 days—under the skin of the left side of the body. In the isolated section the injection sites were controlled for histopathological evaluation.

Clinically the animals showed no signs of an incompatibility during and after the injections.

Macroscopically all injection sites were inconspicuous.

Histopathologically the samples (in each case 2 to 3 tissue sections from different levels of the injection region) showed the following changes:

Isolated alterations which are due to the injection technique (e.g. small hematomas with low grade resorptive cell infiltrate).

Low grade alterations (to be expected) in the sense of a resorption of the test formulation (e.g. small macrophage sites).

No signs of an irritation, independent of the observation period.

Evaluation of the aforementioned composition: subcutaneously compatible having regard to the present results.

Example 5

Testing for the Subcutaneous Compatibility of a CMC Gel with 0.2 mg Ibandronate/g gel Preparation and Filling of the Gel for an Animal Experiment 100 ml of water (water for injection) are placed in a glass beaker and 56.25 mg of ibandronate (hydrate, monosodium salt, corresponding to 50 mg of ibandronate) are dissolved therein while stirring.

Thereafter, 12.5 g of Na carboxymethylcellulose are introduced portionwise and the volume is made up to 250 ml with water. The batch is stirred slowly with a blade stirrer for 24 hours and thereafter left to stand for a further 24 hours in order for the air to disappear.

The gel is then filled into sterilized glass syringes having a flask and rubber plunger, with the fill amount of each syringe being 0.55 g (filling via the cone). The cone of each syringe was sealed with a rubber tip cap.

The filled syringes are stood upright (i.e. with the cone upwards) and sterilized by steam scrubbing in an autoclave. A Pt100 heat conductor placed in the product solution of one syringe is used to control the sterilization time (121–123° C., 20 min., 1 bar gauge pressure).

The syringes are subsequently dried in a sterile room for 12 hours at room temperature under laminar flow and stored sealed in sterilized foil until used.

Compatibility Testing

The local subcutaneous compatibility was tested using 2 male and 2 female rabbits. Each animal was given a total of 3 injections (in each case 0.5 ml/animal)—divided over 7 days—under the skin of the right side of the body. In the isolated section the injection sites were controlled for histopathological evaluation.

Clinically the animals showed no signs of an incompatibility during and after the injections.

Macroscopically all injection sites were inconspicuous.

Histopathologically the samples (in each case 2 to 3 tissue sections from different levels of the injection region) showed the following changes:

Isolated alterations which are due to the injection technique (e.g. small hematomas with low grade resorptive cell infiltrate).

Low grade alterations (to be expected) in the sense of a resorption of the test formulation (e.g. small macrophage sites).

Only slight and isolated signs of an irritation, independent of the observation period (e.g. low grade focal haemorrhages or tissue necroses).

Evaluation of the aforementioned composition: subcutaneously compatible conditionally having regard to the present results.

Example 6

Testing for the Subcutaneous Compatibility of a CMC Gel with the Addition of Calcium Ions Preparation and Filling of the Gel for an Animal Experiment 100 ml of water (water for injection) are placed in a glass beaker and 331.25 mg of $CaCl_2$ $2H_2O$ are dissolved therein while stirring. Thereafter, 12.5 g of Na carboxymethylcellulose are introduced portionwise and the volume is made up to 250 ml with water. The batch is stirred slowly with a blade stirrer for 24 hours and thereafter left to stand for a further 24 hours in order for the air to disappear.

The gel is then filled into sterilized glass syringes having a flask and rubber plunger, with the fill amount of each syringe being 0.55 g (filling via the cone). The cone of each syringe was sealed with a rubber tip cap.

The filled syringes are stood upright (i.e. with the cone upwards) and sterilized by steam scrubbing in an autoclave. A Pt100 heat conductor placed in the product solution of one syringe is used to control the sterilization time (121–123° C., 20 min., 1 bar gauge pressure).

The syringes are subsequently dried in a sterile room for 12 hours at room temperature under laminar flow and stored sealed in sterilized foil until used.

Compatibility Testing

The local subcutaneous compatibility was tested using 4 male and 4 female rabbits. Each animal was given a total of 3 injections (in each case 0.5 ml/animal)—divided over 7 days—under the skin of the left side of the body. In the isolated section the injection sites were controlled for histopathological evaluation.

Clinically the animals showed no signs of an incompatibility during and after the injections.

Macroscopically all injection sites were inconspicuous.

Histopathologically the samples (in each case 2 to 3 tissue sections from different levels of the injection region) showed the following changes:

Isolated alterations which are due to the injection technique (e.g. small hematomas with low grade resorptive cell infiltrate).

Low grade alterations (to be expected) in the sense of a resorption of the test formulation (e.g. small macrophage sites).

No signs of an irritation, independent of the observation period.

Evaluation of the aforementioned composition: subcutaneously compatible having regard to the present results.

Example 7

Testing for the Subcutaneous Compatibility of a CMC Gel with the Addition of Calcium Ions and 0.2 mg Ibandronate/g gel Preparation and Filling of the Gel for an Animal Experiment 100 ml of water (water for injection) are placed in a glass beaker and 56.25 mg of ibandronate (hydrate, monosodium salt, corresponding to 50 mg of ibandronate) as well as 331.25 mg of $CaCl_2 2H_2O$ are dissolved therein while stirring. Thereafter, 12.5 g of Na carboxymethylcellulose are introduced portionwise and the volume is made up to 250 ml with water. The batch is stirred slowly with a blade stirrer for 24 hours and thereafter left to stand for a further 24 hours in order for the air to disappear.

The gel is then filled into sterilized glass syringes having a flask and rubber piston, with the fill amount of each syringe being 0.55 g (filling via the cone). The cone of each syringe was sealed with a rubber tip cap.

The filled syringes are stood upright (i.e. with the cone upwards) and sterilized by steam scrubbing in an autoclave. A Pt100 heat conductor placed in the product solution of one syringe is used to control the sterilization time (121–123° C., 20 min., 1 bar gauge pressure).

The syringes are subsequently dried in a sterile room for 12 hours at room temperature under laminar flow and stored sealed in sterilized foil until used.

Compatibility Testing

The local subcutaneous compatibility was tested using 2 male and 2 female rabbits. Each animal was given a total of 3 injections (in each case 0.5 ml/animal)—divided over 7 days—under the skin of the right side of the body. In the isolated section the injection sites were controlled for histopathological evaluation.

Clinically the animals showed no signs of an incompatibility during and after the injections.

Macroscopically all injection sites were inconspicuous.

Histopathologically the samples (in each case 2 to 3 tissue sections from different levels of the injection region) showed the following changes:

Isolated alterations which are due to the injection technique (e.g. small hematomas with low grade resorptive cell infiltrate).

Low grade alterations (to be expected) in the sense of a resorption of the test formulation (e.g. small macrophage sites).

No signs of an irritation, independent of the observation period.

Evaluation of the aforementioned composition: subcutaneously compatible having regard to the present results.

What is claimed is:

1. A pharmaceutical composition in a dosage form for subcutaneous administration comprising an aqueous gel having a viscosity of $\geq 220$ mPa*s containing as an active ingredient for combating osteoporosis a bisphosphonate acid or its pharmaceutically acceptable salt dissolved in an aqueous solution, and a polymeric gel forming agent capable of inhibiting diffusion of the active ingredient with human tissue, the agent being a natural or synthetic polymer and selected from the group consisting of cellulose derivatives, alginic acid derivatives, dextrans, gelatines, collagen, hyaluronic acids and/or dermatan and heparan sulfates.

2. The composition of claim 1, wherein said natural polymer is a cellulose derivative.

3. The composition of claim 2, wherein said cellulose derivative is a soluble alkyl- or hydroxyalkylcellulose derivative.

4. The composition of claim 3, wherein said alkyl or hydroxy cellulose derivative is selected from the group consisting of hydroxymethylcellulose (HMC), hydroxyethylcellulose (HEC), hydroxypropylcellulose (HPC), methylhydroxyethylcellulose (MHEC), hydroxypropylmethylcellulose (HPMC), carboxymethylcelluose (CMC), methylcellulose (MC) and salt mixtures thereof.

5. The composition of claim 4, wherein said natural polymer is sodium carboxymethylcellulose.

6. The composition of claim 1, wherein said natural polymer is alginate.

7. The composition of claim 1, wherein said agent is a synthetic polymer selected from the group consisting of poly(meth)acrylic acids, poly(meth)acrylates, polyvinylpyrrolidone and polyvinyl alcohol.

8. The composition of claim 1, wherein said aqueous gel has a viscosity of from 380 to 1800 mPa*s.

9. The composition of claim 1, wherein said composition additionally contains 1 to 20 mM of calcium ions.

10. The composition of claim 9, wherein the calcium ions are produced by the presence of calcium chloride in the aqueous solution.

11. The composition of claim 1, wherein the active ingredient is ibandronate, clodronate, etidronate, risedronate, zoledronate, tiludronate, pamidronate, cimadronate (YM 175) and/or alendronate or their sodium or calcium salts.

12. The composition of claim 11, wherein the active substance is 3-(N-methyl-N-pentyl) amino-1-hydroxypropane-1,1-bisphosphonic acid (ibandronic acid) or pharmaceutically acceptable salts thereof.

13. The composition of claim 12, wherein the active substance is 3-(N-methyl-N-pentyl) amino-1-hydroxypropane-1,1-bisphosphonic acid, monosodium salt, monohydrate.

14. A pharmaceutical composition comprising an aqueous gel having a viscosity of $\geq 220$ mPa*s in a unit dosage form suitable for subcutaneous administration to the tissue of human patients, said gel containing as an active ingredient 200–1000 µg of a bisphosphonate acid or its pharmaceutically acceptable salt, which are active in combating osteoporosis dissolved in an aqueous solution, and from about 0.01%–15% by weight based upon the weight of the aqueous gel, of a polymeric gel forming agent capable of inhibiting diffusion with human tissue, the agent being a natural or synthetic polymer gel elected from the group consisting of cellulose derivatives, alginic acid derivatives, dextrans, gelatines, collagen, hyaluronic acids and/or dermatan and heparan sulfates.

15. The composition of claim 14, wherein the composition contains as an active ingredient 200–300 µg of a bisphosphonate acid or its pharmaceutically acceptable salt.

16. The composition of claim 14, wherein said natural polymer is a cellulose derivative.

17. The composition of claim 16, wherein the cellulose derivative is a soluble alkyl- or hydroxyalkylcellulose derivative.

18. The composition of claim 17, wherein the alkyl or hydroxy cellulose derivative is selected from the group consisting of hydroxymethylcellulose (HMC), hydroxyethylcellulose (HEC), hydroxypropylcellulose (HPC), methylhydroxyethylcellulose (MHEC), hydroxypropylmethylcellulose (HPMC), carboxymethylcelluose (CMC), methylcellulose (MC) and salts and mixtures thereof.

19. The composition of claim 18, wherein the natural polymer is sodium carboxymethylcellulose.

20. The composition of claim 14, wherein the natural polymer is alginate.

21. The composition of claim 14, wherein the agent is a synthetic polymer selected from the group consisting of poly(meth)acrylic acids, poly(meth)acrylates, polyvinylpyrrolidone and polyvinyl alcohol.

22. The composition of claim 21, wherein the agent is sodium carboxymethylcellulose (Na CMC) in a concentration of from 1 to 7% by weight based upon the weight of the gel.

23. The composition of claim 22, wherein the sodium carboxymethylcellulose (Na CMC) is present in a concentration from 4 to 6% by weight based upon the weight of the gel.

24. The composition of claim 20, wherein the alginate is present in a concentration of from 1 to 5% by weight based upon the weight of the gel.

25. The composition of claim 24, wherein the alginate is present in a concentration of from 2 to 3% by weight based upon the weight of the gel.

26. The composition of claim 14, wherein the viscosity of the aqueous gel is from 380 to 1800 mPa*s.

27. The composition of claim 14, wherein said composition additionally contains from 1 to 20 mM of calcium ions.

28. The composition of claim 27, wherein said composition of calcium ions are produced by the presence of $CaCl_2$ in the aqueous solution.

29. The composition of claim 14, wherein the active bisphosphonate is ibandronate, clodronate, etidronate, risedronate, zoledronate, tiludronate, pamidronate, cimadronate (YM175) and/or alendronate or their sodium or calcium salts.

30. The composition of claim 29, wherein the bisphosphonate is 3-(N-methyl-N-pentyl) amino-1-hydroxypropane-1,1-bisphosphonic acid (ibandronic acid) or pharmaceutically acceptable salts thereof.

31. The composition of claim 30, wherein the bisphosphonate is 3-(N-methyl-N-pentyl) amino-1-hydroxypropane-1,1-bisphosphonic acid, monosodium salt, monohydrate.

32. The composition of claim 14, wherein it comprises from 200 μg to 1 mg of the active substance or active substance mixture, from 0.5 to 1 mg of a calcium salt and from 15 to 50 mg to of a cellulose derivative or alginate in 1 ml of water.

33. The composition of claim 32, wherein the composition contains 200–300 μg of the active substance or active substance mixture, 0.5 mg of a calcium salt and 15 mg of a cellulose derivative or alginate in 1 ml of water.

34. The composition of claim 33, wherein the composition contains 1 mg of the active substance or active substance mixture, 1 mg of a calcium salt and 50 mg of a cellulose derivative or alginate in 1 ml of water.

35. The composition of claim 14, wherein said composition contains an active substance, a calcium salt and a diffusion inhibiting compound selected from the group consisting of carboxymethylcellulose and alginate.

36. A method for combating osteoporosis comprising subcutaneous administering to the tissue of a human patient an aqueous gel containing a viscosity of ≧220 Pa*s containing as an active ingredient a bisphosphonate acid or its pharmaceutically acceptable salt active in combating osteoporosis and present in said gel in an effective amount to combat osteoporosis and a polymeric gel forming agent capable of inhibiting diffusion of said active ingredient into human tissue, the agent being a natural or synthetic polymer gel selected from the group consisting of cellulose derivatives, alginic acid derivatives, dextrans, gelatines, collagen, hyaluronic acids and/or dermatan and heparan.

37. The method of claim 36, wherein said agent is present in an amount of from 0.01% to 15% by weight based upon the weight of the gel.

38. The method of claim 36, wherein the cellulose derivative is selected from the group consisting of hydroxymethylcellulose (HMC), hydroxyethylcellulose (HEC), hydroxypropylcellulose (HPC), methylhydroxyethylcellulose (MHEC), hydroxypropylmethylcellulose (HPMC), carboxymethylcelluose (CMC), methylcellulose (MC) and salts and mixtures thereof.

39. The method of claim 38, wherein said agent is an alginate.

40. The method of claim 36, wherein said agent is a synthetic polymer selected from the group consisting of poly(meth)acrylic acids, poly(meth)acrylates, polyvinylpyrrolidone and polyvinyl alcohol.

41. The method of claim 38, wherein said agent is sodium carboxymethylcellulose (Na CMC) present in a concentration of 1–7% by weight based upon the weight of the aqueous gel.

42. The method of claim 39, wherein said alginate is present in a concentration of 1–5% by weight based upon the weight of the aqueous gel.

43. The method of claim 36, wherein the viscosity of the gel is from 380 to 1800 mPa*s.

44. The method of claim 36, wherein the active ingredient is ibandronate, clodronate, etidronate, risedronate, zoledronate, tiludronate, pamidronate, cimadronate (YM175) and/or alendronate or their sodium or calcium salts.

45. The method of claim 44, wherein the active ingredient is 3-(N-methyl-N-pentyl) amino-1-hydroxypropane-1,1-bisphosphonic acid (ibandronic acid) or pharmaceutically acceptable salts thereof.

46. The method of claim 36, wherein the unit dosage form contains from 200 to 1 mg of the active ingredient from 0.5 to 1 mg of a calcium salt and 15 to 50 mg of a cellulose derivative or alginate in 1 ml of water.

47. The method of claim 46, wherein the unit dosage form contains 200–300 μg of the active substance or active substance mixture, 0.5 mg of a calcium salt and 15 mg of a cellulose derivative or alginate in 1 ml of water.

48. The method of claim 46, wherein the unit dosage form contains 1 mg of the active substance or active substance mixture, 1 mg of a calcium salt and 50 mg of a cellulose derivative or alginate in 1 ml of water.

* * * * *

UNITED STATES PATENT AND TRADEMARK OFFICE
CERTIFICATE OF CORRECTION

PATENT NO. : 6,676,970 B2
DATED : January 13, 2004
INVENTOR(S) : Rainer Bader et al.

It is certified that error appears in the above-identified patent and that said Letters Patent is hereby corrected as shown below:

<u>Title page,</u>
Item [73], Assignee, delete "Hoffman-La Roche Inc., Nutley, NJ (US)" and insert
-- Hoffmann-La Roche Inc., Nutley, NJ (US) --.
Item [30], Foreign Application Priority Data, delete "May 5, 1922" and insert
-- May 5, 2000 --.

Signed and Sealed this

Twenty-fifth Day of May, 2004

JON W. DUDAS
*Acting Director of the United States Patent and Trademark Office*